United States Patent [19]

Wojtkowski

[11] Patent Number: 4,792,633

[45] Date of Patent: Dec. 20, 1988

[54] PREPARATION OF ORTHO-(ALKYL- OR ARYLTHIO)PHENOLS

[75] Inventor: Paul W. Wojtkowski, Wilmington, DE

[73] Assignee: E. I. Du Pont de Nemours and Company, Wilmington, Del.

[21] Appl. No.: 864,226

[22] Filed: May 19, 1986

[51] Int. Cl.$^4$ ............................................. C07C 148/02
[52] U.S. Cl. ............................................. 568/46; 568/47; 568/48; 568/49; 568/50; 568/52; 568/53; 568/54
[58] Field of Search ............................................. 568/46, 47, 48, 49, 568/52, 53, 54; 560/50

[56] References Cited

U.S. PATENT DOCUMENTS

| | | | |
|---|---|---|---|
| 2,923,743 | 2/1960 | Deffs et al. | 568/54 |
| 3,134,818 | 5/1964 | Farah et al. | 568/54 |
| 4,324,920 | 4/1982 | McKinnie et al. | 568/54 |
| 4,547,593 | 10/1985 | Ranken | 568/54 |
| 4,599,451 | 7/1986 | Wojtkowski | 568/54 |

OTHER PUBLICATIONS

P. Ranken et al., Synthesis, Feb. 1984, pp. 117–119, Alkylthiolation of Phenols.

B. Farah et al., J. Organic Chemistry, vol. 28, pp. 2807–2809 (1963), Alkylmercaptophenols by Sulfenylation of Phenols.

*Primary Examiner*—Mary E. Ceperley

[57] ABSTRACT

Strong acids, e.g., aluminosilicates and sulfonic acids are employed as catalysts for the (alkyl or aryl)thiolation of phenols using dialkyl or diaryl disulfides and/or (alkyl- or arylthio)phenols as thiolating agents, and for the isomerization of (alkyl- or arylthio)phenols, to prepare ortho(alkyl- or arylthio)phenols as the predominant products.

17 Claims, No Drawings

PREPARATION OF ORTHO-(ALKYL- OR ARYLTHIO)PHENOLS

CROSS REFERENCE TO RELATED APPLICATIONS

U.S. Ser. No. 740,030 filed on May 31, 1985 and issued on July 8, 1986 as U.S. Pat. No. 4,599,451 by P. W. Wojtkowski discloses using zirconium phenoxides as catalysts for thiolation.

BACKGROUND OF THE INVENTION

1. Field of the Invention

This invention relates to a process for the preparation of ortho-(alkyl- or arylthio)phenols by using certain amorphous and crystalline aluminosilicates and/or other strong acids as catalysts for the reaction of phenols with dialkyl or diaryl disulfides and/or certain (alkyl- or arylthio)phenols as (alkyl or aryl)thiolating agents, and for the isomerization of (alkyl- or arylthio)phenols.

2. Description of Related Art

Ortho-(alkylthio)phenols are used to prepare agricultural chemicals such as herbicides. U.S. Pat. No. 4,324,920, issued on Apr. 13, 1982 and the article by P. F. Ranken et al. entitled "Alkylthiolation of Phenols", Synthesis, February 1984, pp. 117-9 disclose a process for the preparation of ortho-(alkylthio)phenols along with lesser amounts of para-(alkylthio)phenols by contacting phenols with dialkyl disulfides in the presence of aluminum phenoxide catalysts. U.S. Pat. No. 2,923,743, issued on Feb. 2, 1960, discloses a process for the preparation of ortho-(alkylthio)phenols by contacting phenols with dialkyl disulfides in the presence of at least equimolar quantities of condensation agents, such as aluminum chloride, aluminum bromide, ferric chloride, zince chloride, tin tetrachloride, antimony pentachloride, or boron fluoride. Examples 4 and 5 of the U.S. Pat. No. 2,923,743 show that lesser amounts of ortho-(alkylthio)phenols relative to the para isomers are produced when the condensation agent is a bleaching earth or activated bleaching earth such as Tonsil ®.

It is disclosed in U.S. Pat. No. 3,134,818 issued May 26, 1964, Belgian Pat. No. 626,874, Canadian Pat. No. 714,094, and Journal of Organic Chemistry, 28, 2807 (1963) that the preparation of para-(alkylthio)phenols along with lesser amounts of ortho-(alkylthio)phenols can be effected by reaction of phenols with dialkyl disulfides in the presence of acid catalysts such as phosphoric acid, polyphosphoric acid, concentrated sulfuric acid, alkanesulfonic acid, arenesulfonic acid, and specific cationic ion-exchange resins. U.S. Pat. No. 4,547,593 issued Oct. 15, 1985 discloses the preparation of (hydrocarbylthio)phenols by heating one or more mono- or poly(hydrocarbylthio)phenols in the presence of aluminum phenoxide catalysts to redistribute the starting materials.

SUMMARY OF THE INVENTION

A process for the preparation of relatively high levels of ortho-(hydrocarbylthio)phenols, e.g. ortho(alkyl-or arylthio)phenols, by reacting at a temperature in the range 50°-250°, preferably 110°-220°, and for a sufficient period of time to maximize the desired ortho isomer, phenols, having at least one unsubstituted ortho-position, with a hydrocarbyl disulfide such as methyl disulfide, and/or with a (hydrocarbylthio)phenol, such as para-(methylthio)phenol, or by reacting para-(hydrocarbylthio)phenols by themselves, in the presence of strong acids such as crystalline zeolitic aluminosilicates, mixed metal oxides including especially amorphous silica-aluminas, clays, sulfuric or phosphoric acids, alkyl- or aryl-sulfonic acids, polymer-supported sulfonic acids, zirconium phenoxides, or boron trifluoride and mixtures of the foregoing.

DETAILED DESCRIPTION OF THE INVENTION

The phenols to be thiolated in this process include phenol itself, catechol, resorcinol, and polynuclear phenols such as naphthols. The aryl portion of the phenol may be linked to or fused with other cyclic systems, including heterocyclic systems such as those containing cyclo oxygen, nitrogen, or sulfur rings. In addition to hydroxyl, other substituents which do not interfere with the reaction can be present on the phenol as long as at least one orthoposition remains unsubstituted. Suitable substituents include $C_1$-$C_6$ alkyl groups, Cl, F, I, Br, $OR_1$, aryl, or aryl substituted with $C_1$-$C_6$ alkyl groups, Cl, F, I, Br, $OR_1$ and where $R_1$ is $C_1$-$C_6$ alkyl groups or phenyl. The preferred phenols are phenol, 4-chlorophenol, and 4-methylphenol. Operable phenols are identified by the formula

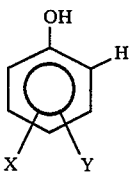

wherein

X and Y are independently selected from the group consisting of H, OH, $C_1$-$C_6$ alkyl, $OR_1$, Cl, F, I, Br, aryl, or aryl substsituted with $C_1$-$C_6$ alkyl, $OR_1$, Cl, F, I or Br, or when X and Y are on adjacent carbon atoms, they may be taken together to form $CH=CH-CH=CH$; and $R_1$ is $C_1$-$C_6$ alkyl or phenyl;

provided that X and Y cannot simultaneously be OH, and when X or Y is OH and the other is hydrogen, the OH cannot be in the para position.

Thiolating agents usable in this invention include dialkyl and diaryl disulfides, i.e., having the formula $(RS)_2$. The dialkyl disulfides which are operable in the present invention include those where the alkyl group has 1-6 carbon atoms but when the alkyl groups contain 4-6 carbon atoms the carbon bonded to the heteroatom must be substituted by one or two hydrogen atoms. Dimethyl disulfide, diethyl disulfide and di-n-propyl disulfide are preferred.

Diaryl disulfides which are operable include those wherein the aryl group is unsubstituted or substituted with one or more substituents including $C_1$-$C_6$ alkyl, Cl, F, I, Br, $OR_1$, aryl where $R_1$ is $C_1$-C6 alkyl or phenyl.

The term hydrocarbyl as used herein means the alkyl groups and aryl groups in the above-described disulfides. The term (hydrocarbylthio)phenols used herein includes mono-(hydrocarbylthio)phenols which can be the ortho, meta, and para isomer, di-(hydrocarbylthio)phenols, and poly-(hydrocarbylthio)phenols.

Other alkylthiolating agents which can be used singly or in combination with disulfides include (alkylthio)phenols, preferably para-(alkylthio)phenols or di-(alkylthio)phenols, preferably where the alkyl groups are the same as in the dialkyl disulfide described above. (Arylthio)phenols, preferably para-(arylthio)phenols or di(arylthio)phenols, can also be used as arylthiolating agents for the preparation of ortho-(arylthio)phenols, and can have aryl the same as in the diaryl disulfide described above. In the case of all disubstituted phenols as alkylthiolating or arylthiolating agents, the preferred isomers are the ortho,ortho- and ortho,para-.

The mixed metal oxides operable as catalysts in the present invention possess sufficient acidity to be catalytically active for alkyl- or arylthiolation. A discussion of mixed metal oxides and their acidity along with examples is given in K. Tanabe, *Solid Acids and Bases,* Academic Press, 1970, Chapter 4. The most preferred mixed metal oxides in this invention are amorphous aluminosilicates also referred to as amorphous silica-aluminas or simply silica-aluminas. The amorphous aluminosilicates are the simplest form of aluminosilicates.

Neither silica nor alumina have a strong acidic character. However, in silica-aluminas, the isomorphous replacement of some tetravalent silicon ions with trivalent aluminum ions in the tetrahedral silica structure creates acidic sites necessary for catalytic activity in the silica-aluminas. The addition of a small amount of water will govern whether these are Lewis or Bronsted acid sites, and both may be present. Heating a silica-alumina can increase its acidity, for example by lowering its water content since excess water can compete for absorption sites. More complete descriptions of the structure and acidity of silica-aluminas can be found in the articles by B. C. Gates et al. entitled "*Chemistry of Catalytic Processes*" (McGraw-Hill, 1979, Chapter 1) and L. H. Little entitled "*Infrared Spectra of Adsorbed Species*" (Academic Press. 1966, Chapter 7). A wide range of silica-aluminas can be used in this invention provided they have sufficient acidity to be catalytically active for alkyl- or arylthiolation. The alumina content can vary from 5 to 90%, but the preferred silica-aluminas contain 10–60% and more preferably 25–30% alumina. The amorphous silica-aluminas can be combined with other matrix materials, e.g., clay, which does not hinder the catalytic activity under process conditions. The silica-aluminas can be treated under appropriate conditions including atmosphere, time and temperature to improve or restore their catalytic activity.

Another group of materials which are operable in the present invention include the crystalline alumino-silicates (zeolites) which are conveniently represented by the formula:

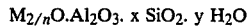

$M_{2/n}O \cdot Al_2O_3 \cdot x\, SiO_2 \cdot y\, H_2O$ wherein M is a cation of valence n, x $\geq$ 2, and y is a number determined by the porosity and the hydration state of the zeolite, generally from 2 to 8. In naturally-occurring zeolites, M is principally represented by Na, Ca, K, Mg and Ba in proportions usually reflecting their approximate geochemical abundance. The cations M are loosely bound to the structure and can frequently be completely or partially replaced with other cations by conventional ion exchange.

These zeolite structures are characterized by corner-linked tetrahedra with Al or Si atoms at centers of tetrahedra and oxygen atoms at corners. Such tetrahedra are combined in a well-defined repeating structure comprising various combinations of 4-, 6-, 8-, 10-, and 12-membered rings. The resulting framework consists of regular channels and cages, which impart a useful pore structure of catalysis. Pore dimensions are determined by the geometry of the aluminosilicate tetrahedra forming the zeolite channels or cages, with nominal openings of 2.6 Å for 6-rings, 4.0 Å for 8-rings, 5.5 Å for 10-rings and 7.4 Å for 12 rings. Pore dimension is related to catalytic performance, since this characteristic determines whether reactant molecules can enter and product molecules can exit the zeolite framework. In practice, it has been observed that very slight decreases in ring dimensions can effectively hinder or block movement of particular reactants or products within a zeolite structure.

Useful references generally relating to zeolite structure and characterization include the following:

Meier et al., *Atlas of Zeolite Structure Types* (International Zeolite Assn. 1978);

Mumpton, "Natural Zeolites" in *Reviews in Mineralogy* 14:1 (1977);

Smith, "Origin and Structure of Zeolites" in *Zeolite Chemistry and Catalysis,* ACS Monograph 171 (American Chemical Society, 1976).

The preferred zeolite is zeolite Y, a large-pore synthetic zeolite with a nominal Si/Al ratio of 2.4 which can be described by the formula

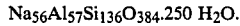

$Na_{56}Al_{57}Si_{136}O_{384} \cdot 250\, H_2O$.

The structure and synthesis of this synthetic zeolite are described in *Zeolite Molecular Sieves,* by D. W. Breck, John Wiley, 1974.

The crystal structure of zeolite Y is characterized by large 26-hedron cages with 12-ring openings, defining pore sizes of approximately 7.4 Å (0.74 nm) which permits entrance of branched-chain hydrocarbons and aromatic molecules.

The cationic species Na$^+$ present in Y zeolites can be exchanged for protons in a conventional ion exchange with H$^+$ or by conversion to an ammoniated form (NH$_4$Y) which is subsequently converted to the acid form by calcination at elevated temperatures.

An acid form of zeolite Y can also be prepared by introduction of a trivalent ion such as La$^{3+}$ or other rare earth ion. An example of such rare-earth exchanged Y zeolites is known as SK-500 produced by the Union Carbide Co.

Of particular utility for the process of the present invention are Si-rich forms of zeolite Y. Examples of such zeolites are commercial zeolites such as ELZ-10 (Si/Al=2.97) or ELZ-20 (Si/Al=3.12) produced by the Union Carbide Co.

Another zeolite employed in the present invention is the high silica zeolite Beta described in U.S. Pat. No. 3,308,069 and U.S. Pat. No. Re. 28,341. The Si/Al ratio varies from about 5 to 50. The crystal structure of zeolite Beta is not known, but sorption measurements showing a capacity of 20% cyclohexane indicated it to be a large pore zeolite and Martens et al., Zeolites, 4, 98 (1984) find, from the conversion of n-decane over H, Pt Beta, that Beta is a large-pore zeolite with 12-membered rings and moderately sized cages.

Another zeolite useful in this invention is mordenite which can be described by the formula

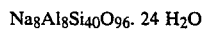

$Na_8Al_8Si_{40}O_{96} \cdot 24\, H_2O$

The crystal structure of mordenite is characterized by parallel channels running along the c-axis and having a cross section of 6.7×7.0 Å (0.67–0.70 nm). These parallel channels are joined by smaller channels which are not accessible to large organic molecules such as those having aromatic ring structures.

Medium-pore high-silica zeolites known generally as pentasil zeolites and specifically as ZSM-5 and ZSM-11 are also preferred and are described in U.S. Pats. Nos. 3,702,886, and 3,709,979, the articles by Kokotailo et al., *The Properties and Applications of Zeolites,* Chem. Soc. Spec. Publ. No. 33, London (1979), and Olson et al., J. Catalysis 61, 390 (1980). These groups of zeolites are identified by the formula:

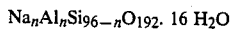

where n usually varies from 0 to about 8. The structures of both ZSM-5 and ZSM-11 contain intersecting channels made up of 10-membered rings having cross sections, pore sizes, of 5–6 Å (0.5–0.6 nm). The configuration of the channels is not critical to the activity, e.g., the ZSM-5 structure contains zig-zag channels intersecting straight channels. The pore size of ZSM-5 reduces the formation of di- and highersubstituted (alkylthio)phenols because they are bulkier than the monosubstituted phenols and consequently have more difficultly forming in the channels.

Other medium-pore zeolites with pores defined by either 10- or 12-membered rings such as offretite, ferrierite, ZSM-34, ZSM-23, and ZSM-35 are operable as catalysts. Small pore zeolites, such as erionite, whose channels are constructed of 8-rings are not preferred because the phenolic moieties are too large to enter the channels which are less than about 5 Å and usually of the order of 4 Å (0.4 nm).

Acid forms of zeolites are preferred in this invention. Acid forms of zeolites can be prepared by a variety of techniques including ammonium exchange followed by calcination, direct exchange of alkali ions for protons using mineral acids or ion exchangers, and by introduction of polyvalent ions (for a discussion of acid sites in zeolites, see J. Dwyer, "Zeolite Structure, Composition and Catalysis" in *Chemistry and Industry,* Apr. 2, 1984). The acid sites produced are generally believed to be of the Bronsted (proton donating) type or of the Lewis (electron pair accepting) type. Bronsted sites are generally produced by deammoniation at low temperatures, exchange with protons, or hydrolysis of polyvalent cations. Lewis sites are believed to arise from dehydroxylation of the H zeolites or from the presence of polyvalent ions. In the acidic zeolite catalysts of the present invention, Bronsted and/or Lewis sites can be present.

It has previously been established (Kerr, "Hydrogen Zeolite Y, Ultrastable Zeolite Y, and Aluminum-Deficient Zeolites", in *Molecular Series, Advances in Chemistry Series* 121:210 (American Chemical Society (1973)) that NH$_4$ zeolites deammoniated by deepbed calcination techniques exhibit properties distinct from those of zeolites deammoniated by shallow-bed calcination techniques. Deep-bed calcination refers to combinations of bed geometry and calcination conditions, e.g., thick beds and/or slow flow of gas over zeolite, which do not result in rapid removal of gaseous N$_2$O and NH$_3$ from the heated zeolite. In contrast, shallow-bed calcination refers to bed geometries and conditions, e.g., shallow beds and rapid stripping of gases from the bed, which maximize removal of H$_2$O and NH$_3$ from zeolite. Deep bed conditions are preferred.

The nature of the differences between acid forms of zeolites as prepared by the above-described techniques has not been precisely pinpointed. It has been suggested, however, that products of deep-bed calcination conditions contain nonframework Al species which have dissociated from the zeolite lattice during the deammoniation process. Freude et al., *Zeolites* 3:171 (1983) have shown that, according to temperature and the degree of deep-bed calcination of zeolite NH$_4$ Y, nonframework Al species containing octahedrally-coordinated Al are progressively condensed. Presumably such nonframework species function as catalytically active sites or as modifiers of other catalyticallyactive sites. Such "deep-bed" calcined zeolites are particularly advantageous for the present invention and generally preferred over "shallow-bed" calcined zeolites, but both types of catalysts will work in the present invention.

Generally, calcination temperatures must be sufficiently high to convert substantially all NH$_4^+$ sites to H$^+$ sites and other acid sites, yet not high enough to render significant amounts of the zeolite amorphous. The presence of NH$_4^+$ in a given sample can be determined by infrared measurements. Excessive calcination can lead to collapse of zeolite crystalline structure and an amorphous state, which is to be distinguished from "X-ray amorphous" zeolitic materials.

In practicing the process of the invention, the zeolite catalysts of the invention can be combined with another material resistant to the temperature and other conditions employed in the process. Such matrix materials include synthetic or natural substances such as clays, silica and metal oxides.

The number and strength of acid sites are major factors in catalytic activity and are related to the aluminum content of zeolites. Minimum Al content corresponds to Si/Al ratio of about 1000.

As a measure of acid strength, Miale et al., J. Catal. 6,278 (1966) have used the cracking of n-hexane to determine alpha values. In this test, zeolites are compared in their ability to convert 12.5% n-hexane passed as saturated vapor (25° C.) in a stream of helium over the catalyst at 538° C. with a 9 second superficial contact time at a time of 5 minutes after commencing flow.

The table below compares alpha values obtained from a wide variety of zeolites. The preferred catalysts of this invention H ZSM-5, H Y, H mordenite and H Beta are all observed to have high alpha values, indicating that one of the characteristics of the zeolite catalyst of this invention is their strong acidity.

| Alpha Values for Zeolite Catalysts | |
| --- | --- |
| Zeolite | Alpha Value |
| ZSM-11 | 40–200 |
| ZSM-23 | 310 |
| ZSM-35 | 420 |
| ZSM-34 | 150–900 |
| La Y | 700 |
| H Y | 1200 |
| H Beta | 1000–20,000 |
| H Mordenite | >100,000 |
| H ZSM-5 | >100,000 |

The use of aluminosilicates, both amorphous and crystalline, provide advantages over catalysts described in the prior art in the predominant production of the ortho-isomer in synthetically useful amounts. Aluminosilicates are not as corrosive as the commonly used acids such as sulfuric, and are therefore safer and easier to handle. Most are commercially available. The aluminosilicate catalysts are not as moisture sensitive as other materials such as aluminum phenoxide. Certain of the aluminosilicates provide reaction rates higher than certain prior-art catalysts. The aluminosilicates are essentially insoluble and can be readily separated from the reaction mixture by simple, inexpensive filtration, and can be reused directly or regenerated if necessary. They can also be employed in fixed beds.

The formation of lower amounts of unwanted di- and higher-substituted (hydrocarbylthio)phenols, which are common by-products of these reactions, can be effected by choice of a zeolite aluminosilicate catalyst of appropriate pore size. Additional advantages of the process in this invention include, that the unwanted (hydrocarbylthio)phenol isomers such as para-(hydrocarbylthio)phenol and di-(hydrocarbylthio)phenol by-products, which are normally formed in the reaction, can be recycled to shift the products to the desired ortho-isomer. The generation of large amounts of malodorous mercaptan by-products, which are common in the prior art using disulfides as thiolating agents, can be avoided by the use of (hydrocarbylthio)phenols, especially para-(hydrocarbylthio)phenols or di-(hydrocarbylthio)phenols, as the thiolating agents.

Other catalysts, besides the above-described crystalline zeolitic aluminosilicates and mixed metal oxides including especially amorphous silica-alumina usable in this invention, depending upon starting materials, are strong acids such as clays, sulfuric acid, phosphoric acid, polyphosphoric acid, alkyl- or arylsulfonic acids, polymer-supported sulfonic acids, boron trifluoride and zirconium phenoxides.

Clays can be of a wide variety such as montmorillonites, bentonites, etc. The clays are preferably activated before use by treatment with acid, for example by boiling in a dilute mineral acid such as sulfuric or hydrochloric acid and then drying.

Examples of the various alkyl- and arylsulfonic acids include trifluoromethanesulfonic acid and p-toluenesulfonic acid. Examples of polymer-supported sulfonic acids include the crosslinked polystyrene cationic ion-exchange resin sold as Amberlyst ® 15, and the perfluorinated ion-exchange resin sold as Nafion ®.

The H+ form of the polymer-supported sulfonic acids is preferred. It has been speculated that when sulfuric acid is used it reacts with a phenol to form an arylsulfonic acid which serves as the catalyst.

Boron trifluoride can be used as is, or as a complex such as boron trifluoride diethyl etherate. Zirconium phenoxides preferably are fully substituted with the phenoxide corresponding to the phenol being reacted but can be partially substituted with alkoxy or halide groups. For example, the preferred form of this catalyst when phenol is a reactant is zirconium tetraphenoxide.

In one preferred embodiment of the process of this invention the phenol, having at least one unsubstituted ortho-position, is reacted with a dialkyl or diaryl disulfide, as thiolating agent in the presence of a catalyst, preferably an amorphous aluminosilicate having about 25% alumina or a crystalline zeolitic aluminosilicate with pores defined by 10- or 12-membered rings and pore size $>\sim 5$ Å at temperatures in the range 110°–220° C. for a sufficient period of time to allow formation of the maximum amount of the desired ortho-isomer. Normally para-, di-, and higher-substituted-(hydrocarbylthio)phenols are also formed in this process, albeit in lesser final amounts than the ortho-isomer. In the case of phenol itself, these di-(hydrocarbylthio)phenols are typically the 2,4- and 2,6-isomers. If dialkyl disulfide is used, provision should be made to allow for the continuous removal of the alkyl mercaptan by-product corresponding to the dialkyl disulfide used. The use of an essentially inert solvent is optional and preferably excess phenol is employed as a solvent reactant. The reaction is normally performed at or below atmospheric pressure under an inert atmosphere. Anhydrous conditions are not necessary, although excessive amounts of moisture which can interfere with the desired reaction are avoided. The product can be isolated by conventional methods including fractional distillation of the total reaction product before or preferably after separation of any solids therein.

In another preferred embodiment of this invention, ortho-(hydrocarbylthio)phenols are obtained by reacting a phenol unsubstituted in at least one ortho position with a thiolating agent which is a (hydrocarbylthio)phenol, preferably a para-(hydrocarbylthio)phenol, and/or an ortho,ortho- and/or ortho,paradi(hydrocarbylthio)phenol, in the presence of the above-described aluminosilicates, clays, mixed metal oxides besides aluminosilicates, alkyl- or arylsulfonic acids, polymer-supported sulfonic acids, sulfuric, phosphoric, or polyphosphoric acids, boron trifluoride, or zirconium phenoxides in which the phenoxide is the same as the phenol to be thiolated. An example is the reaction of phenol itself with a para-(alkylthio)phenol to yield ortho-(alkylthio)phenol wherein the reaction is allowed to proceed at elevated temperature for the period of time which yields the maximum amount of the desired ortho-isomer.

In another preferred embodiment of this invention, ortho-(hydrocarbylthio)phenols are obtained by reacting a phenol unsubstituted in at least one ortho position with a mixture of dihydrocarbyl disulfide and (hydrocarbylthio)phenols, including para- and/or ortho,ortho-di- and/or ortho,para-di-, in the presence of as catalysts aluminosilicates, mixed metal oxides besides aluminosilicates, clays, alkyl- or arylsulfonic acids, polymer-supported sulfonic acids, boron trifluoride, or zirconium phenoxides to produce improved yields of ortho-(hydrocarbylthio)phenols based on the phenol and disulfide used. The hydrocarbylthio groups of all thiolating agents should be the same. Provision should be made to allow by-product hydrocarbylmercaptan to escape. An example is the reaction of phenol itself with dimethyl disulfide in the presence of para-(methylthio)phenol and di-(methylthio)phenols to produce more ortho-(methylthio)phenol than in their absence.

In another embodiment of this invention, (hydrocarbylthio)phenol, especially para-(hydrocarbylthio)phenol, is isomerized to ortho-(hydrocarbylthio)phenol in the presence of aluminosilicates, mixed metal oxides other than aluminosilicates, clays, sulfuric or phosphoric acids, alkyl- or arylsulfonic acids, polymersupported sulfonic acids, boron trifluoride, or zirconium phenoxides where the phenoxide corresponds to the phenol of the (hydrocarbylthio)phenols.

This reaction is performed by contacting the para-(hydrocarbylthio)phenol with the catalyst, preferably an aluminosilicate, and heating at temperatures in the range 110°–220° C. for a sufficient period of time to allow formation of the maximum amount of the desired ortho-isomer. The reaction is normally performed at or below atmospheric pressure under an inert atmosphere. Anhydrous conditions are not necessary, although excessive amounts of moisture which can interfere with the reaction are avoided. The product can be isolated by conventional methods as described earlier.

The overall results in all the above reactions produces mono-ortho-(hydrocarbylthio)phenols in greater amounts than para-(hydrocarbylthio)phenols or di-(hydrocarbylthio)phenols when formation of all these isomers is possible, i.e., is not prevented by substitution on the phenol starting material.

In the course of these processes, a small amount of higher-substituted-(hydrocarbylthio)phenols are normally produced also. if the mon-substituted phenol is desired, the amount of di- and higher(hydrocarbylthio)-phenols produced can be lowered by starting with an excess of the phenol to be hydrocarbylthiolated. The amount of di- or higher-(alkylthio)phenols can also be reduced by using a zeolitic catalyst of a pore size e.g., 5-6 Angstrom units, which will restrict formation of the larger disubstituted products.

The processes of the present invention are normally conducted at temperatures of 50°-250° C., usually 110°-220°C., and preferably at 120°-180° C. The molar ratio of phenol to thiolating agent is 5:1 to 1:3, preferably 3:1 to 1:1. The amount of catalyst used may cover a wide range depending upon the activity of the particular catalyst used. The aluminosilicates, other mixed metal oxides, polymersupported sulfonic acids, and clays are generally used at catalytic levels in amounts of 100 grams to 1 gram per mole of thiolating agent, or preferably 75 g/mole to 5 g/mole, or more preferably 50 g/mole to 10 g/mole. The alkyl- or arylsulfonic acid catalysts, zirconium phenoxide catalysts, and sulfuric or phosphoric acid catalysts are generally used in molar ratios of catalyst to thiolating agent of 0.5 to 0.01 or preferably 0.2 to 0.05. Boron trifluoride is used in catalytic amounts, i.e., less than equimolar, relative to the thiolating agent. Polymer-supported sulfonic acid catalysts can be recovered from a reaction mixture and regenerated by known techniques. Zeolitic catalysts can be regenerated e.g., by calcining in air at 550° C. for about 4 hours.

The following Examples are presented to illustrate but not to restrict the present invention.

EXAMPLE 1

A 25 ml round bottom, glass flask fitted with a condenser, nitrogen inlet, thermometer and stirring mechanism was charged with 1.0 g phenol, 1.0 g methyl disulfide and 0.5 g H Y zeolite (LZ-Y82 obtained from Union Carbide Co. heated 4 hr at 575° C. in flowing nitrogen). The contents of the flask were covered with a nitrogen blanket and heated until reflux at which time the temperature of the contents was approximately 110° C. The temperature gradually increased during the reaction. After reflux was established, samples of the liquid contents of the flask were removed periodically with a pipette and analyzed by gas chromatography (GC). The results are reported in Table I.

TABLE I

| Time | % Area | | | |
| (Hours) | | (Methylthio)phenols | | |
| | Phenol | Ortho | Para | Disubstituted |
| 1 | 61 | 9 | 20 | 0 |
| 3 | 54 | 15 | 22 | 2 |
| 5 | 48 | 22 | 22 | 5 |

TABLE I-continued

| Time | % Area | | | |
| (Hours) | | (Methylthio)phenols | | |
| | Phenol | Ortho | Para | Disubstituted |
| 9 | 46 | 30 | 15 | 9 |
| 11 | 46 | 31 | 15 | 8 |

EXAMPLE 2

Approximately 3.0 g of para-(methylthio)phenol along with 1.0 g of H Y (Example 1) zeolite were charged to the apparatus of Example 1. The liquid contents of the flask were sampled and analyzed as described in Example 1 with the following results reported in Table II.

TABLE II

| Time | Temperature | % Area | | | |
| (Hours) | (°C.) | | (Methylthio)phenols | | |
| | | Phenol | Ortho | Para | Disubstituted |
| 2 | 140 | 17.0 | 2.7 | 75.5 | 14.2 |
| 5 | 168 | 25.0 | 18.4 | 28.7 | 25.6 |
| 8 | 170 | 23.6 | 26.1 | 16.8 | 31.8 |
| 12 | 170 | 28.6 | 32.7 | 15.5 | 18.9 |

EXAMPLE 3

The apparatus of Example 1 was charged with 1.9 g phenol, 9.4 g phenyl disulfide and 1.0 g H Y zeolite (Example 1) and the contents heated under nitrogen at relfux temperatures of 128°-138° C. for 22 hours following which the liquid contents were analyzed by gas chromatography. The following compounds in corresponding area were detected: phenol (16%), phenyl disulfide (27%), ortho-(phenylthio)phenol (19%) and para(phenylthio)phenol (10%).

EXAMPLES 4-13

With reference to Table III, the apparatus of Example 1 was charged with the indicated amount of phenol, methyl disulfide and catalyst and the contents heated under nitrogen at the indicated temperatures and time following which the liquid contents were analyzed by gas chromatography. The results are reported in Table III.

In Examples 4 and 7, amorphous silica-alumina was obtained from the Davison Chemical Division, W. R. Grace Co., Grade 980-25, 25% Al$_2$O$_3$.

In Example 5, Type Y Zeolite LZ-Y82 (NH$_4$Y) which is a large-pore zeolite with 12-ring openings defining pore sizes of approximately 7.4 Å was obtained from the Union Carbide Co. and heated 4 hours at 575° C. in flowing nitrogen to form H Y zeolite.

In Example 6, H ZSM-5 which is a medium-pore zeolite with 10-ring channels having cross sections of approximately 5-6 Å was prepared by calcination of 10 g of NH$_4$ ZSM-5 in a covered crucible at 550° C. for 10 hours.

In Example 13, the clay is Mineral Colloid BP Montmorillonite from George Kaolin Co. refluxed for 1 hour in 5% hydrochloric acid, filtered, washed with water several times, and dried in a vacuum oven at 110° C.

In Example C$_1$, silica was obtained from the Aldrich Chemical Co., sold as silica gel, SiO$_2$ (Merck, 35-70 mesh) 40 Å, surface area 675 m$_2$/g, pore volume 0.68 cm$^3$/g equivalent to Merck 10181.

In Example C$_2$, gamma-alumina was prepared by heating Catapal SB (obtained from Conoco, Inc.) at 700° C. for 15 hours.

In Example C$_3$, H Erionite which is a small-pore zeolite with 8-ring channels having cross sections of approximately 4 Å was prepared by calcination of 50 g of "Linde" natural erionite (E10, Union Carbide Co.) at 500° C. for 10 hours in flowing nitrogen, three exchanges in 10% NH$_4$NO$_3$ solution, and a final calcination in flowing nitrogen at 500° C. for 10 hours.

W. R. Grace Co.) was heated in stagnant air at 390° C. for one hour prior to use.

In Example 15, the catalyst was a rare earth exchanged Type Y zeolite identified as SK-500 and obtained from Union Carbide Corp.

In Example 16, H mordenite was prepared by heating NH$_4$ mordenite, LZ-M-8, obtained from Union Carbide Co., at 500° C. in a covered crucible for 16 hours.

In Example 17, Zeolite ZSM-5 was prepared from a mixture of 7.20 g Na aluminate, 9.60 g NaOH, 128.0 g of

TABLE III

| Example No. | Reactants Phenol (grams) | Disulfide (grams) | Catalyst Type | Amount (grams) | Reaction Conditions Temperature (°C.) | Time (hours) | % Area Phenol | (Methylthio)phenols Ortho | Para | Disubstituted | Higher-Substituted |
|---|---|---|---|---|---|---|---|---|---|---|---|
| 4[a] | 2.0 | 2.0 | Silica-Alumina | 1.0 | 130 | 24 | 38.4 | 32.6 | 11.9 | 14.4 | 0.3 |
| 5[a] | 2.0 | 2.0 | H Y Zeolite | 1.0 | 130 | 22 | 37.3 | 27.3 | 15.3 | 13.2 | 6.8 |
| 6[a] | 2.0 | 2.0 | H ZSM-5 | 1.0 | 130 | 21 | 38.5 | 32.3 | 24.6 | 2.7 | 1.5 |
| 7 | 1.0 | 1.5[b] | Silica-Alumina | 1.0 | 130 | 24 | 62.3 | 20.7 | 14.9 | 2.0 | ND |
| 8 | 1.0 | 1.5[b] | Conc. H$_2$SO$_4$ | 0.2 | 130 | 4 | 57.5 | 22.2 | 14.8 | 5.5 | ND |
| 9 | 2.0 | 3.0[b] | BF$_3$ Diethyl Etherate | 0.5 | 170[c] | 22 | 44.3 | 15.1 | 11.9 | NA | NA |
| 10 | 2.0 | 3.0[b] | 85% Phosphoric Acid | 0.5 | 170[c] | 22 | 47.0 | 22.2 | 13.6 | NA | NA |
| 11 | 2.0 | 3.0[b] | Polyphosphoric Acid | 0.5 | 170[c] | 22 | 49.4 | 21.1 | 16.9 | NA | NA |
| 12 | 1.2 | 3.0[b] | Zirconium Tetraphenoxide | 1.0 | 175[c] | 4 | 53.7 | 19.8 | 10.7 | NA | NA |
| 13 | 4.0 | 6.0[b] | Clay | 2.0 | 175 | 27 | 54.4 | 20.0 | 9.8 | NA | NA |
| C$_1$[a] | 2.0 | 2.0 | Silica | 1.0 | 130 | 23.5 | 100 | 0 | 0 | 0 | 0 |
| C$_2$[a] | 2.0 | 2.0 | Gamma-Alumina | 1.0 | 130 | 21 | 100 | 0 | 0 | 0 | 0 |
| C$_3$[a] | 2.0 | 2.0 | H Erionite | 1.0 | 130 | 22 | 100 | 0 | 0 | 0 | 0 |

[a]Contents heated for 2 hours at about 105-115° C. before indicated conditions
[b]Para-(methylthio)phenol was used instead of methyl disulfide
[c]Contents heated for 24 hours at 135° C. before indicated conditions
NA = Not Analyzed
ND = None Detected
C = Comparative

EXAMPLES 14–26

With reference to table IV, the indicated amounts of phenol, methyl (unless otherwise noted) disulfide, and the catalyst were combined and heated under nitrogen at reflux while allowing alkyl mercaptan corresponding to the disulfide used to escape and the temperature to increase. The reaction was terminated at the indicated temperatures and heating times which generally correspond in these and other examples to the point where not further products formed and gas chromagraphic analysis indicated no further increases in the amount of mono-ortho-(alkylthio)phenol product. The reaction mixture was then permitted to cool to room temperature and then filtered. The remaining solids were thoroughly washed with ether. The washings and initial filtrate were combined and volatiles and removed on a rotary flash evaporator following which the nonvolatiles were analyzed by gas chromatography. The results are reported in Table IV.

In Example 14, amorphous silica-alumina (25% Al$_2$O$_3$, Grade SMR7-S198, Davison Chemical Division, a 50% solution of tetrapropylammonium bromide, 480.0 g Ludox HS-30 colloidal SiO$_2$ and 528.0 g H$_2$O heated in a Hastelloy C autoclave at 140° C. for 24 hours. The product, after washing, filtering and drying, was identified by X-ray diffraction as the pentasil ZSM-5. The acid form, H ZSM-5, was prepared by heating the ZSM-5 in flowing air to 500° C. for 10 hours, exchanging three times in 10% NH$_4$NO$_3$ at 80° C., and heating the product NH$_4$ ZSM-5 to 540° C. for 10 hours in flowing N$_2$. For Example 18, this catalyst was heated at 550° C. for 4 hours in a mixture of flowing steam (200 cc/hr H$_2$O) and N$_2$ (1000 cc/min), i.e., shallow-bed conditions, to produce steamed H ZSM-5.

NH$_4$ ELZ-10 was prepared for Examples 19–24 by contacting 50 g of "Linde" Na ELZ-10, a Y zeolite obtained from the Union Carbide Co. having a typical Si/Al ratio of 2.97, four times with a 10% NH$_4$NO$_3$ solution at ~80° C. with filtering in between exchanges to produce NH$_4$ ELZ-10. NH$_4$ ELZ-10 was heated slowly in a covered crucible from 25° to 500° C. and held at 500° C. for 16 hours, i.e., deep-bed conditions, to produce H ELZ-10.

Amorphous silica-alumina in Examples 25 and 26 is that used in Table III.

TABLE IV

| Example No. | Reactants Phenol (grams) | Disulfide (grams) | Catalyst Type | Amount (grams) | Reaction Conditions Temperature (°C.) | Time (hours) | Reaction Mixture Phenol (grams) | (Alkylthio)phenols Ortho- (grams-% yield) | Para- (grams) | Di- (grams) |
|---|---|---|---|---|---|---|---|---|---|---|
| 14 | 6.3 | 4.2 | Silica-Alumina | 1.25 | 184 | 9 | 2.4 | 2.5-40 | 1.1 | 1.1 |
| 15 | 12.5 | 8.4 | SK-500 | 2.5 | 188 | 10 | 4.9 | 3.7-29 | 2.2 | 1.3 |
| 16 | 12.5 | 8.4 | H Mordenite | 2.5 | 181 | 6.5 | 5.3 | 4.0-32 | 2.6 | 1.0 |
| 17 | 12.5 | 8.4 | H ZSM-5 | 2.5 | 171 | 7 | 5.6 | 3.7-30 | 2.5 | 0.2 |

TABLE IV-continued

| Example No. | Reactants | | Catalyst | | Reaction Conditions | | Reaction Mixture | | | |
|---|---|---|---|---|---|---|---|---|---|---|
| | | | | | | | | (Alkylthio)phenols | | |
| | Phenol (grams) | Disulfide (grams) | Type | Amount (grams) | Temperature (°C.) | Time (hours) | Phenol (grams) | Ortho- (grams-% yield) | Para- (grams) | Di- (grams) |
| 18 | 12.5 | 8.4 | Steamed H ZSM-5 | 2.5 | 182 | 13 | 5.4 | 4.5-36 | 3.0 | 0.5 |
| 19 | 25 | 16.8 | H ELZ-10 | 5.0 | 184 | 7 | 10.9 | 10.5-42[a] | NA | NA |
| 20 | 12.5 | 8.4 | H ELZ-10 | 2.5 | 195 | 7[b] | 5.0 | 5.4-43 | 2.3 | 2.3 |
| 21 | 25 | 8.4 | H ELZ-10 | 2.5 | 181 | 7 | 15.9 | 6.5-52 | 3.3 | 0.5 |
| 22 | 12.5 | 8.4 | H ELZ-10[c] | 2.7 | 190 | 8 | 5.1 | 5.0-40 | 2.3 | 2.0 |
| 23 | 12.5 | 8.4 | H ELZ-10[d] | 2.7 | 140 | 6 | 9.3 | 2.1-17 | 1.0 | 1.0 |
| 24 | 10.0 | 6.7 | H ELZ-10[e] | 2.4 | 171 | 4 | 4.0 | 3.8-38 | 2.1 | 0.9 |
| 25 | 12.5 | 10.9[f] | Silica-Alumina | 2.5 | 181 | 16.5 | 4.3 | 5.1-37 | NA | NA |
| 26 | 12.5 | 13.4[g] | Silica-Alumina | 2.5 | 180 | 24.5 | 4.1 | 5.4-36 | NA | NA |

[a]The reaction mixture was vacuum distilled directly without removal of catalyst through a 5" Vigreux column and 22.3 gms of distillate were collected at 95–150° C. at 30 mm Hg and analyzed by gas chromatography which indicated only two major components.
[b]Further heating at 175° C. produced no further reaction.
[c]Recovered from Example 20 - no additional treatment.
[d]Recovered from Example 22 - no additional treatment.
[e]Recovered from Example 23 - regenerated by heating in air at 500° C. for 16 hours.
[f]Ethyl disulfide.
[g]n-Propyl disulfide.
NA = Not Analyzed.

EXAMPLE 27

Preparation of ortho-(Methylthio)phenol

NH₄ ELZ-20 was prepared by contactng 50 g of "Linde" Na ELZ-20, obtained from the Union Carbide Co., four times with a 10% NH$_4$NO$_3$ solution at ~80° C. with filtering in between exchanges to produce NH$_4$ ELZ-20. NH$_4$ ELZ-20 was heated slowly in a covered crucible from 25° to 500° C. and held at 500° C. for 16 hours, i.e., deep-bed conditions, to produce H ELZ-20.

Phenol (12.5 g, 0.13 moles), methyl disulfide (8.4 g, 0.089 moles), and H ELZ-20 (2.5 g) were combined and heated under nitrogen at reflux for 3 hours during which the temperature increased to 180° C. and GC analysis indicated no further increase in the amount of ortho-(methylthio)phenol. Methyl mercaptan was allowed to escape continuously. The mixture was cooled to room temperature and filtered. The catalyst was washed several times with ether and allowed to dry leaving solid weighing 3.2 g. The filtrate and ether washings were combined, and volatiles were removed on a rotary flash evaporator leaving 15.2 g of liquid. GC analysis indicated the presence of phenol (5.3 g, 43% recovered), ortho-(methylthio)phenol (5.1 g, 41% yield), para-(methylthio)phenol (2.3 g), and di(methylthio)phenols (2.2 g).

The reaction above was repeated using identical amounts of phenol and methyl disulfide and 2.9 g of the solid H ELZ-20 catalyst recovered from the reaction above. This mixture was heated and followed by GC as above.

The reaction was stopped after 4 hours at which time the temperature was 174° C. Work-up as before yielded recovered catalyst weighing 2.9 g and 15.4 g of liquid products. GC analysts indicated the presence of phenol (5.3 g, 43% recovered), ortho-(methylthio)phenol (5.0 g, 40% yield), para-methylthio)phenol (1.9 g) and di-(methylthio)phenols (2.2 g).

The reaction was again repeated using identical amounts of phenol and methyl disulfide and 2.8 g of the solid H ELZ-20 catalyst recovered from the first repetition. The mixture was heated for 4 hours at which time the temperature was 179° C. After work-up as before, GC analysis indicated the presence of phenol (5.7 g, 46% recovered), ortho-(methylthio)phenol (5.1 g, 41% yield), para-(methylthio)phenol (2.7 g), and di-(methylthio)phenols (2.4 g).

EXAMPLE 28

Preparation of ortho-(Methylthio)phenol

Zeolite Beta was prepared by heating a mixture of 11.6 g Na aluminate, 116 mL tetraethylammonium (TEA) hydroxide and 290.7 g of Ludox LS colloidal SiO$_2$ in an autoclave at 150° C. for 6 days according to U.S. Pat. No. 3,308,069 issued on May 7, 1967. The product after washing, filtering and drying at 110° C. was identified by X-ray diffraction as TEA Beta. The acidic form, H Beta, was prepared by exchanging three times in 10% NH$_4$NO$_3$ solution and heating the filtered and dried product at 1° C./min to 540° C. for 10 hours.

Phenol (12.5 g, 0.13 moles), methyl disulfide (8.4 g, 0.089 moles), and H Beta (2.5 g) were combined and heated under nitrogen at reflux while methyl mercaptan was allowed to escape continuously. Periodic analysis by GC is shown in Table V.

TABLE V

| | | | % Areas | | | |
|---|---|---|---|---|---|---|
| | | Methyl | | (Methylthio)phenols) | | |
| Time, Hr. | T, °C. | Disulfide | Phenol | Ortho | Para | Di |
| 0 | 120 | 6.6 | 93.4 | 0 | 0 | 0 |
| 1.5 | 146 | 3.1 | 53.8 | 16.8 | 25.5 | 0.8 |
| 6.5 | 184 | 0.5 | 48.8 | 23.8 | 12.6 | 12.1 |
| 8.0 | 180 | 0 | 47.9 | 20.6 | 13.1 | 13.6 |

The mixture was cooled to room temperature and filtered. The catalyst was washed several times with ether and allowed to dry. The filtrate and ether washings were combined, and volatiles were removed on a rotary flash evaporator. GC analysis indicated the presence of phenol (5.3 g. 42% recovered), ortho(methylthio)phenol (5.2 g. 41% yield), para-(methylthio)phenol (2.0 g, and di-(methylthio)phenols (2.0 g).

EXAMPLES 29 AND 30

Preparation of 2-(Methylthio-4-substituted phenols

Amorphous silica-alumina (2.5 g, 25% Al$_2$O$_3$, Grade 980-25, Davison Chemical Division, W. R. Grace Co.), 4-substituted phenol (Table below), and methyl disulfide (8.4 g, 0.089 moles) were combined and heated at reflux under nitrogen for 11–11.5 hours during which temperature increased to 180° C. Methyl mercaptan was allowed to escape continuously. The mixture was cooled to room temperature and filtered. The catalyst was washed several times with ether. The filtrate and ether washings were combined, and volatiles were removed on a rotary flashed evaporator. GC analysis indicated the presence of only two major components, i.e., the 4-substituted phenol starting material and 2-methylthio-4-substituted phenol in the yields indicated in Table VI.

TABLE VI

| | | | 4-Substituted Phenol Products | |
|---|---|---|---|---|
| | Reactant Phenol | | Starting Material | 2-Methyl-thio- |
| Example | 4-Substituent | grams | grams, % recovered | grams, % yield |
| 29 | Cl | 17.1 | 8.8, 52 | 7.4, 44 |
| 30 | CH$_3$ | 14.4 | 6.3, 44 | 10.6, 77 |

EXAMPLE 31

Preparation of ortho-(Methylthio)phenol

Para-(methylthio)phenol (4.0 g, 0.029 moles) and H ELZ-20 from Example 27 (1.0 g) were combined and heated under nitrogen for 15 hours at 168°–177° C. The mixture was filtered and the catalyst was washed with ether several times. The filtrate and ether washings were combined, and volatiles were removed on a rotary flash evaporator. GC analysis indicated the presence of phenol, ortho-(methylthio)phenol, para-(methylthio)phenol, and di-(methylthio)phenols in a 1.5:2.0:1.0:1.5 molar ratio, respectively. The yield of ortho-(methylthio)phenol was 21%.

EXAMPLES 32–34

Preparation of ortho-(Methylthio)phenol

Phenol (4.0 g, 0.043 moles), para-(methylthio)phenol (6.0 g, 0.043 moles), and catalyst (2.0 g, Examples 32 and 33 in Table below) were combined and heated under nitrogen for the times and at the temperatures indicated. The mixtures were cooled to room temperature and filtered. The solid catalyst was washed several times with ether. The filtrate and ether washings were combined, and volatiles were removed on a rotary flash evaporator. GC analysis indicated the presence of phenol, ortho-(methylthio)phenol, para-(methylthio)phenol, and di-(methylthio)phenols. Yields of ortho-(methylthio)phenol are given in the Table below.

In Example 34, phenol (4.0 g), para-(methylthio)phenol (6.0 g), and p-toluenesulfonic acid hydrate (0.8 g) were combined and reacted as above for the time and temperature given in the Table below. The mixture was worked-up and analyzed as in Example 26 above. Yield of ortho-(methylthio)phenol is given in Table VII below.

TABLE VII

| Example | Catalyst | Time, Hr. | T, °C. | o-(Methylthio)phenol, % Yield |
|---|---|---|---|---|
| 33 | H ELZ-20 | 8 | 175 | 46 |
| 33 | Amberlyst ® 15 | 7 | 172 | 47 |
| 34 | p-Toluenesulfonic Acid | 6.5 | 173 | 44 |

EXAMPLE 35

Preparation of 2-Methylthio-4-methylphenol p-Cresol (1.2 g, 0.01 mole), para-(methylthio)phenol (3.0 g, 0.02 mole), and H ELZ-20 from Example 27 (1.0 g) were combined and heated at 176° C. for 14 hours. The mixture was cooled to room temperature and filtered. The catalyst was washed several times with ether. The filtrate and ether washings were combined, and volatiles were removed on a rotary flash evaporator. GC analysis indicated the presence of 2-methylthio-4-methylphenol (0.9 g, 56% yield).

EXAMPLE 36

Preparation of ortho-(Methylthio)phenol

Phenol (25.0 g, 0.27 moles), methyl disulfide (16.8 g, 0.18 moles), and H ELZ-20 from Example 27 (5.0 g) were combined and heated under nitrogen at reflux for 4.5 hours during which the temperature increased to 189° C. and GC analysis indicated no further increase in the amount of ortho-(methylthio)phenol. Methyl mercaptan was allowed to escape continuously. The mixture was cooled to room temperature and filtered. The catalyst was washed with ether several times. The filtrate and ether washings were combined and vacuum distilled through a 5" Vigreux column collecting a fraction weighting 18.5 g that distilled at 98°–167° C. at 30 mm mercury. GC analysis of this fraction indicated only two major components, phenol (8.5 g, 34% recovered) and ortho-(methylthio)phenol (8.8 g, 35% yield). GC analysis indicated that the undistilled portion (9.6 g) was almost entirely para-(methylthio)phenol and di-(methylthio)phenols. The undistilled portion (9.6 g) was combined with phenol (6.6 g, 0.07 moles) and catalyst from the previous reaction (6.8 g), and heated at 175° C. for 6 hours. Additional H ELZ-20 (2.0 g) was added and the mixture was heated for an additional 18 hours at 175° C. The mixture was cooled to room temperature and filtered. The catalyst was washed with ether several times. The filtrate and ether washings were combined, and volatiles were removed on a rotary flash evaporator. GC analysis indicated the presence of phenol (4.6 g), ortho-(methythio)phenol (3.8 g), para(methylthio)phenol (2.0 g), and di-(methythio)phenol (2.8 g).

EXAMPLE 27

Preparation of ortho-(Methylthio)phenol

The undistilled portion from Example 19 (including catalyst) was combined with phenol (17.5 g, 0.19 moles), methyl disulfide (7.5 g, 0.08 moles), and amorphous silica-alumina (5.0 g, 25% Al$_2$O$_3$, Grade 980-25, Davison Chemical Division, W. R. Grace Co.). The mixture was heated a total of 14 hours during which the temperature increased to 180° C. The mixture was cooled to room temperature, filtered, and the catalyst washed with ether several times. The filtrate and ether washings were combined, and volatiles were removed on a rotary flash evaporator. GC analysis indicated the presence of phenol (9.0 g, 51% recovered based on phenol added above), ortho-(methylthio)phenol (8.4 g, 75% based on methyl disulfide used above), para-(methylthio)phenol (2.1 g), and di-(methylthio)phenols (4.6 g).

I claim:
1. A process for the preparation of ortho(alkylthio- or arylthio)phenols wherein the alkylthio- and arylthio- moieties are of the formula RS-which comprises reacting a corresponding phenol having the formula

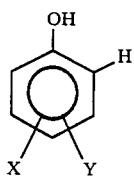

wherein
X and Y are independently selected from the group consisting of H, OH, $C_1$-$C_6$ alkyl, $OR_1$, Cl, F, I, Br, aryl or aryl substituted with $C_1$-$C_6$ alkyl, $OR_1$, Cl, F, I or Br, or when X and Y are on adjacent carbon atoms, they may be taken together to form CH=CH—CH=CH; and
$R_1$ is $C_1$-$C_6$ alkyl or phenyl;
provided that X and Y cannot simultaneously be OH, and when X or Y is OH and the other is hydrogen, the OH cannot be in the para position;
with a compound selected from the group consisting of alkyl or aryl disulfides having the formula $(RS)_2$
wherein R is $C_1$-$C_6$ alkyl or aryl wherein aryl is unsbustituted or substituted with one or more substituents selected from the group consisting of $C_1$-$C_6$ alkyl, Cl, F, I, Br, $OR_1$, aryl where $R_1$ is $C_1$-$C_6$ alkyl or phenyl
provided that when R is $C_4$-$C_6$ alkyl, the carbon bonded to the heteroatom must be substituted by one or two hydrogen atoms; or (alkylthio- or arylthio)phenols, or mixtures of the foregoing wherein the alkylthio- and arylthio- moieties are of the formula RS- and the phenol moieties correspond to Formula I above in the presence of an aluminosilicate having catalytically active acidic sites.

2. The process of claim 1 wherein the resulting ortho(alkylthio- or arylthio)phenols are selected from the group consisting of ortho,ortho-di(alkylthio- or arylthio)phenols; orthi,para-di(alkylthio-or arylthio)phenols; ortho-(alkylthio- or arylthio)phenols and mixtures of the foregoing.

3. The process of claim 1 wherein the alumino-silicate is amorphous and has an alumina content of 5–90% by weight based upon the weight of the silicate.

4. The process of claim 1 wherein the alumino-silicate is amorphous and has an alumina content of 10–60% by weight based upon the weight of the silicate.

5. The process of claim 1 wherein the alumino-silicate is amorphous and has an alumina content of 25–30% by weight based upon the weight of the silicate.

6. The process of claim 2 wherein the alumino-silicate is amorphous and has an alumina content of 5–90% by weight based upon the weight of the silicate.

7. The process of claim 2 wherein the alumino-silicate is amorphous and has an alumina content of 10–60% by weight based upon the weight of the silicate.

8. The process of claim 2 wherein the alumino-silicate is amorphous and has an alumina content of 25–30% by weight based upon the weight of the silicate.

9. The process of claim 1 wherein the alumino-silicate is a zeolite.

10. The process of claim 9 wherein the zeolite is a H zeolite having a pore size greater than about 5 Å.

11. The process of claim 2 wherein the zeolite is a H zeolite having a pore size greater than about 5 Å.

12. The process of claim 11 wherein the zeolite has a Si/Al ratio in the range of about 2.4 to 1000.

13. The process of claim 12 wherein the zeolite is prepared by calcining an $NH_4$ zeolite under deep bed conditions.

14. The process of claim 1 wherein the alumino-silicate is an H Y zeolite.

15. The process of claim 1 wherein the alumino-silicate is an H Beta zeolite.

16. The process of claim 1 wherein the alumino-silicate is an H ZSM-5 zeolite.

17. The process of claim 1 wherein the alumino-silicate is an H mordenite zeolite.

* * * * *